(12) United States Patent
Paulson et al.

(10) Patent No.: US 6,399,336 B1
(45) Date of Patent: Jun. 4, 2002

(54) PRACTICAL IN VITRO SIALYLATION OF RECOMBINANT GLYCOPROTEINS

(75) Inventors: James C. Paulson, Del Mar; Robert J. Bayer; Eric Sjoberg, both of San Diego, all of CA (US)

(73) Assignee: Neose Technologies, Inc., Horsham, PA (US)

( * ) Notice: Subject to any disclaimer, the term of this patent is extended or adjusted under 35 U.S.C. 154(b) by 0 days.

(21) Appl. No.: 09/007,741

(22) Filed: Jan. 15, 1998

Related U.S. Application Data

(60) Provisional application No. 60/035,710, filed on Jan. 16, 1997.

(51) Int. Cl.[7] .............................. C12P 1/00; C12P 21/06; C12P 19/00; G01N 33/53; C12Q 1/00
(52) U.S. Cl. .............................. 435/97; 435/4; 435/7.2; 435/15; 435/41; 435/183; 435/193; 435/252.3; 435/220
(58) Field of Search ............................. 435/4, 15, 252.3, 435/254.1, 254.3, 7.2, 41, 97, 183, 193, 220

(56) References Cited

U.S. PATENT DOCUMENTS

| | | |
|---|---|---|
| 5,047,335 A | 9/1991 | Paulson et al. |
| 5,272,066 A | 12/1993 | Bergh et al. |
| 5,541,083 A | 7/1996 | Paulson et al. |

FOREIGN PATENT DOCUMENTS

| | | |
|---|---|---|
| WO | WO 92/16640 | 10/1992 |
| WO | WO 94/25615 | 11/1994 |

OTHER PUBLICATIONS

M.C. Field et al., *Glycobiology* (1995) 5(5): 463–472.
A. Harduin–Lepers et al., *Glycobiology* (1995) 5(8): 741–758.
M. Kono et al., *Glycobiology* (1997) 7(4): 469–479.
M.A. Williams et al., *Glycoconjugate Journal* (1995) 12: 755–761.
L. Borsig et al., *Biochemical and Biophysical Research Communications* (May 5, 1995) 210(1): 14–20.
M. Gilbert et al., *The Journal of Biological Chemistry* (Nov. 8, 1996) 271 (45): 28271–28276.
C.F. Goochee et al., "The Oligosaccharides of Glycoproteins: Bioprocess Factors Affecting Oligosaccharide Structure and Their Effect on Glycoprotein Properties," *Review*, Dept. of Chemical Engineering, Stanford Univ., Stanford, CA.
D.H. Joziasse et al., *Journal of Biological Chemistry* (Jan. 25, 1985) 260(2) 714–719.
D.H. Joziasse et al., *Journal of Biological Chemistry* (Feb. 15, 1987) 262(5): 2025–2033.
J.C. Paulson et al., *The Journal of Biological Chemistry* (Apr. 10, 1977) 252(7) 2363–2371.
S. Tsuji et al., *Glycobiology* (1996) 6(7): v–xiv.
A. Varki, *Glycobiology* (1992) 2(1): 25–40.
J. Weinstein et al., *The Journal of Biological Chemistry* (Nov. 25, 1982) 257(22): 13845–13853.
T. Yamamoto et al., *J. Biochem.* (1996) 120: 104–110.
Goochee et al. *Bio/Technology* (1991) 9: 1347–1355.
Wen et al. *J. Biol. Chem.* (1992) 267: 21011.
Van den Eijnden et al. *J. Biol. Chem.* (1981) 256: 3159.
Sasaki et al. *J. Biol. Chem* (1993) 268: 22782–22787.
Kitagawa & Paulson *J. Biol. Chem.* (1994) 269: 1394–1401.
Kitagawa et al. *J. Biol. Chem.* (1996) 271: 931–938.
Paulson et al. *J. Biol. Chem.* (1978) 253: 5617–5624.
Wallenfels et al. *Meth Enzymol.* (1966) 9: 112–116.

*Primary Examiner*—Ponnathapu Achutamurthy
*Assistant Examiner*—Manjunath N. Rao
(74) *Attorney, Agent, or Firm*—Townsend and Townsend and Crew LLP

(57) ABSTRACT

This invention provides methods for practical in vitro sialylation of glycoproteins, including recombinantly produced glycoproteins. The methods are useful for large-scale modification of sialylation patterns.

87 Claims, 2 Drawing Sheets

PRACTICAL IN VITRO SIALYLATION OF RECOMBINANT GLYCOPROTEINS

CROSS-REFERENCE TO RELATED APPLICATIONS

This application claims priority to U.S. Provisional Application No. 60/035,710, filed Jan. 16, 1997, which is incorporated herein by reference in its entirety for all purposes.

BACKGROUND OF THE INVENTION

1. Field of the Invention

This invention pertains to the field of in vitro sialylation of glycoproteins, including recombinant glycoproteins.

2. Background

The circulatory lifetime of glycoproteins in the blood is highly dependent on the composition and structure of its N-linked carbohydrate groups. This fact is of direct relevance for therapeutic glycoproteins which are intended to be administered parenterally. In general, maximal circulatory half life of a glycoprotein requires that its N-linked carbohydrate groups terminate in the sequence NeuAc-Gal-GlcNAc. Without the terminal sialic acid (NeuAc), the glycoprotein is rapidly cleared from the blood by a mechanism involving the recognition of the underlying N-acetylgalactosamine (GalNAc) or galactose (Gal) residues (Goochee et al. (1991) *Biol/Technology* 9: 1347–1355). For this reason, ensuring the presence of terminal sialic acid on N-linked carbohydrate groups of therapeutic glycoproteins is an important consideration for their commercial development.

In principle, mammalian cell culture systems used for production of most therapeutic glycoproteins have the capacity to produce glycoproteins with fully sialylated N-linked carbohydrate groups. In practice, however, optimal glycosylation is often difficult to achieve. Under the conditions of large scale production, overproduction of the glycoprotein by the cell can outstrip its ability to keep up with glycosylation, and this capability can be positively and negatively influenced by many subtle variables in culture conditions (Goochee et al., supra.).

Production of glycoproteins in transgenic animals has some of the same problems as mammalian cell culture. While the "production" of a glycoprotein is inherently better controlled, it is also less susceptible to manipulation. If glycosylation is not complete, there is little that can be done with the animals to alter the outcome. With transgenic animals there is often another problem. While the predominant sialic acid in humans is N-acetyl-neuraminic acid (NeuAc), goats, sheep and cows all produce a large fraction of their total sialic acid as N-glycolyl-neuraminic acid (NeuGc). Although the impact of this modification is not yet fully explored from a functional or regulatory perspective, it is known that the NeuGc substitution is antigenic in humans (Varki (1992) *Glycobiology* 2: 25–40).

Since the most important problems associated with glycosylation of commercially important recombinant and transgenic glycoproteins, involve terminal sialic acid, a need exists for an in vitro procedure to enzymatically "cap" carbohydrate chains that lack a terminal sialic acid. With such a procedure, the problem encountered with transgenic glycoproteins could also be addressed by resialylation with NeuAc once the "non-human" sialic acid NeuGc was removed. The ideal method would employ a sialyltransferase that is capable of efficiently sialylating N-linked or O-linked oligosaccharides of recombinant glycoproteins on a practical scale. The present invention fulfills these and other needs.

SUMMARY OF THE INVENTION

The present invention provides methods for in vitro sialylation of saccharide groups present on a recombinantly produced glycoprotein. The methods comprise contacting the saccharide groups with a sialyltransferase, a sialic acid donor moiety, and other reactants required for sialyltransferase activity for a sufficient time and under appropriate conditions to transfer sialic acid from the sialic acid donor moiety to said saccharide group.

In a preferred embodiment, the methods are carried out using sialyltransferase at a concentration of about 50 mU per mg of glycoprotein or less, preferably between about 5–25 mU per mg of glycoprotein. Typically, the concentration of sialyltransferase in the reaction mixture will be between about 10–50 mU/ml, with the glycoprotein concentration being at least about 2 mg/ml of reaction mixture. In a preferred embodiment, the method results in sialylation of greater than about 80% of terminal galactose residues present on said saccharide groups. Generally, the time required to obtain greater than about 80% sialylation is less than or equal to about 48 hours.

Sialyltransferases that are useful in the methods of the invention typically have a sialyl motif that comprises about 48–50 amino acids, within which about 40% of the amino acids are identical to the consensus sequence RCAVVSSAG - - - DVGSKT (SEQ ID NO:1)(where - - - indicates a variable number of amino acid residues such that the motif is about 48–50 residues in length). Examples of sialyltransferases that are suitable for use in the present invention include ST3Gal III (preferably a rat ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al. (1996) *Glycobiology* 6: v–xiv). The methods of the invention can involve sialylation of recombinant glycoproteins with more than one sialyltransferase; for example, with an ST3 Gal III and an ST3Gal I, or an ST3 Gal III and an ST6 Gal I, or other combinations of enzymes. The sialic acid donor moiety used in the claimed methods is generally CMP-sialic acid, which can be added to the reaction directly or can be enzymatically generated in situ. The sialic acids used in a preferred embodiment are selected from the group consisting of NeuAc and NeuGc.

The invention also provides a glycoprotein having an altered sialylation pattern, wherein terminal galactose residues of said glycoprotein are sialylated using the claimed methods.

DETAILED DESCRIPTION

Definitions

Figure 1:
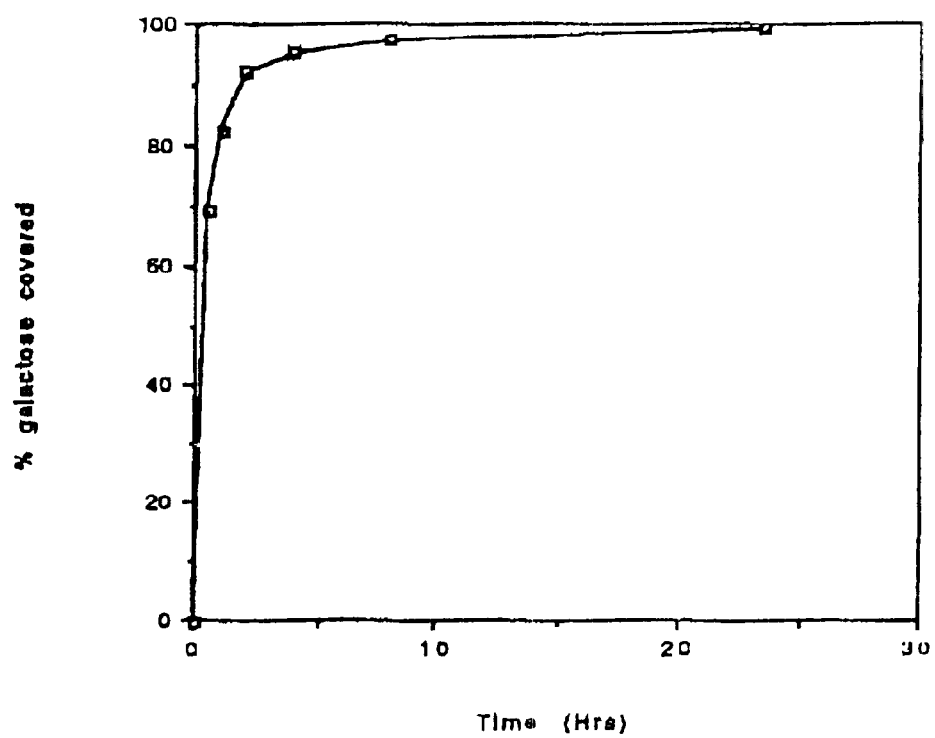
FIG. 1 shows a time course of ST3Gal III-mediated sialylation of α1-acid glycoprotein which had been treated with neuraminidase. The percentage of terminal galactose residues which are sialylated is plotted versus the time of reaction.

The following abbreviations are used herein:

Ara=arabinosyl;
Fru=fructosyl;
Fuc=fucosyl;
Gal=galactosyl;

GalNAc =N-acetylgalactosaminyl;
Glc=glucosyl;
GlcNAc=N-acetylglucosaminyl;
Man=mannosyl; and
NeuAc=sialyl (typically N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond ($\alpha$ or $\beta$), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose.

The term "sialic acid" refers to any member of a family of nine-carbon carboxylated sugars. The most common member of the sialic acid family is N-acetylneuraminic acid (2-keto-5-acetamindo-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550–11557; Kanamori et al. (1990) *J. Biol. Chem.* 265: 21811–21819. Also included are 9-substituted sialic acids such as a 9-O-$C_1$–$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki (1992) *Glycobiology* 2: 25–40; *Sialic Acids: Chemistry, Metabolism and Function*, R. Schauer, Ed. (Springer-Verlag, N.Y. (1992)). The synthesis and use of sialic acid compounds in a sialylation procedure is disclosed in international application WO 92/16640, published Oct. 1, 1992.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant polypeptide" is one which has been produced by a recombinant cell.

A "heterologous sequence" or a "heterologous nucleic acid", as used herein, is one that originates from a source foreign to the particular host cell, or, if from the same source, is modified from its original form. Thus, a heterologous glycoprotein gene in a eukaryotic host cell includes a glycoprotein gene that is endogenous to the particular host cell that has been modified. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated" is meant to refer to material which is substantially or essentially free from components which normally accompany the enzyme as found in its native state. Typically, isolated molecules are at least about 80% pure, usually at least about 90%, and preferably at least about 95% pure as measured by, e.g., band intensity on a silver stained gel or other method for determining purity. Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The practice of this invention can involve the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well-known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Suitable host cells for expression of the recombinant polypeptides are known to those of skill in the art, and include, for example, eukaryotic cells including insect, mammalian and fungal cells. In a preferred embodiment, *Aspergillus niger* is used as the host cell.

Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; Van Brunt (1990) *Biotechnology* 8: 291–294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039.

DESCRIPTION OF THE PREFERRED EMBODIMENTS

The present invention provides methods for efficient in vitro sialylation of saccharide groups attached to glycoproteins, in particular recombinantly produced glycoproteins. For example, the methods of the invention are useful for sialylation of recombinantly produced therapeutic glycoproteins that are incompletely sialylated during production in mammalian cells or transgenic animals. The methods involve contacting the saccharide groups with a sialyltransferase and a sialic acid donor moiety for a sufficient time and under appropriate reaction conditions to transfer sialic acid from the sialic acid donor moiety to the saccharide groups. Sialyltransferases comprise a family of glycosyltransferases that transfer sialic acid from the donor substrate CMP-sialic acid to acceptor oligosaccharide substrates. In preferred embodiments, the sialyltransferases used in the methods of the invention are recombinantly produced.

The methods of the invention are useful for altering the sialylation pattern of glycoproteins. The term "altered" refers to the sialylation pattern of a glycoprotein as modified using the methods of the invention being different from that observed on the glycoprotein as produced in vivo. For example, the methods of the invention can be used to produce a glycoprotein having a sialylation pattern that is different from that found on the glycoprotein when it is produced by cells of the organism to which the glycoprotein is native. Alternatively, the methods can be used to alter the sialylation pattern of glycoproteins that are recombinantly produced by expression of a gene encoding the glycoprotein in a host cell, which can be of the species from which the glycoprotein is native, or from a different species.

Recombinant glycoproteins that have sialylation patterns that are modified by the methods of the invention can have important advantages over proteins that are in their native, unaltered glycosylation state, or that are in a glycosylation state that is less than optimal for a particular application. Such non-optimal sialylation patterns can arise when a recombinant glycoprotein is produced in a cell that does not have the proper complement of glycosylation machinery to produce the desired glycosylation pattern. The optimal or preferred glycosylation pattern may or may not be the native glycosylation pattern of the glycoprotein when produced in its native cell. Advantages of optimal sialylation patterns include, for example, increased therapeutic half-life of a glycoprotein due to reduced clearance rate. Altering the sialylation pattern can also mask antigenic determinants on foreign proteins, thus reducing or eliminating an immune response against the protein. Alteration of the sialylation of a glycoprotein-linked saccharide can also be used to target a protein to a cell surface receptor that is specific for the altered oligosaccharide, or to block targeting to a receptor that is specific for the unaltered saccharide.

Proteins that can be modified by the methods of the invention include, for example, hormones such as insulin, growth hormones (including human growth hormone and bovine growth hormone), tissue-type plasminogen activator (t-PA), renin, clotting factors such as factor VIII and factor IX, bombesin, thrombin, hemopoietic growth factor, serum albumin, receptors for hormones or growth factors, interleukins, colony stimulating factors, T-cell receptors, MHC polypeptides, viral antigens, glycosyltransferases, and the like. Polypeptides of interest for recombinant expression and subsequent modification using the methods of the invention also include α1-antitrypsin, erythropoietin, granulocyte-macrophage colony stimulating factor, antithrombin III, interleukin 6, interferon β, protein C, fibrinogen, among many others. This list of polypeptides is exemplary, not exclusive. The methods are also useful for modifying the sialylation patterns of chimeric proteins, including, but not limited to, chimeric proteins that include a moiety derived from an immunoglobulin, such as IgG.

The in vitro sialylation methods provided by the invention are, unlike previously described sialylation methods, practical for commercial-scale production of modified glycoproteins. Thus, the claimed methods provide a practical means for large-scale preparation of glycoproteins having altered sialylation patterns. The methods are well suited for therapeutic glycoproteins that are incompletely sialylated during production in mammalian cells or transgenic animals. The processes provide an increased and consistent level of terminal sialylation of a glycoprotein.

One way by which the methods of the invention achieve commercial feasibility is through the use of recombinantly produced sialyltransferases. Recombinant production enables production of sialyltransferases in the large amounts that are required for large-scale glycoprotein modification. Deletion of the membrane anchoring domain of sialyltransferases, which renders sialyltransferases soluble and thus facilitates production and purification of large amounts of sialyltransferases, can be accomplished by recombinant expression of a modified gene encoding the sialyltransferase. Examples of recombinant sialyltransferases, including those having deleted anchor domains, as well as methods of producing recombinant sialyltransferases, are found in, for example, U.S. Pat. No. 5,541,083. At least 15 different mammalian sialyltransferases have been documented, and the cDNAs of thirteen of these have been cloned to date (for the systematic nomenclature that is used herein, see, Tsuji et al. (1996) *Glycobiology* 6: v–xiv). These cDNAs can be used for recombinant production of sialyltransferases, which can then be used in the methods of the invention.

Commercial practicality is also provided by the methods of the invention through the use of bacterial sialyltransferases, either recombinantly produced or produced in the native bacterial cells. Two bacterial sialyltransferases have been recently reported; an ST6Gal II from *Photobacterium damsela* (Yamamoto et al. (1996) *J. Biochem.* 120: 104–110) and an ST3Gal V from *Neisseria meningitidis* (Gilbert et al. (1996) *J. Biol. Chem.* 271: 28271–28276). The two recently described bacterial enzymes transfer sialic acid to the Galβ1,4GlcNAc sequence on oligosaccharide substrates. However, there are no known bacterial proteins that are glycosylated, so it was unknown whether or not the Galβ1,4GlcNAc moiety covalently linked to a protein would serve as an acceptor substrate for a bacterial sialyltransferase. Table 1 shows the acceptor specificity of these and other sialyltransferases useful in the methods of the invention.

In preferred embodiments, the methods of the invention are commercially practical due to the use of sialyltransferases that are capable of sialylating a high percentage of acceptor groups on a glycoprotein using a low ratio of enzyme units to glycoprotein. In a preferred embodiment, the desired amount of sialylation will be obtained using about 50 mU of sialyltransferase per mg of glycoprotein or less. More preferably, less than about 40 mU of sialyltransferase will be used per mg of glycoprotein, even more preferably, the ratio of sialyltransferase to glycoprotein will be less than or equal to about 45 mU/mg, and more preferably about 25 mU/mg or less. Most preferably, the desired amount of sialylation will be obtained using less than about 10 mU/mg sialyltransferase per mg glycoprotein. Typical reaction conditions will have sialyltransferase present at a range of about 5–25 mU/mg of glycoprotein, or 10–50 mU/ml of reaction mixture with the glycoprotein present at a concentration of at least about 2 mg/ml.

Typically, the saccharide chains on a glycoprotein having sialylation patterns altered by the methods of the invention will have a greater percentage of terminal galactose residues sialylated than the unaltered glycoprotein. Preferably, greater than about 80% of terminal galactose residues present on the glycoprotein-linked saccharide groups will be sialylated following use of the methods. More preferably, the methods of the invention will result in greater than about 90% sialylation, and even more preferably greater than about 95% sialylation of terminal galactose residues. Most preferably, essentially 100% of the terminal galactose residues present on the glycoprotein are sialylated following modification using the methods of the present invention. The methods are typically capable of achieving the desired level of sialylation in about 48 hours or less, and more preferably in about 24 hours or less.

Preferably, for glycosylation of N-linked carbohydrates of glycoproteins the sialyltransferase will be able to transfer sialic acid to the sequence Galβ1,4GlcNAc-, the most common penultimate sequence underlying the terminal sialic acid on fully sialylated carbohydrate structures. Only three of the cloned mammalian sialyltransferases meet this acceptor specificity requirement, and each of these have been demonstrated to transfer sialic acid to N-linked carbohydrate groups of glycoproteins. Examples of sialyltransferases that use Galβ1,4GlcNAc as an acceptor are shown in Table 1.

TABLE I

Sialyltransferases which use the Galβ1,4GlcNAc sequence as an acceptor substrate.

| Sialyltransferase | Source | Sequence(s) formed | Ref. |
|---|---|---|---|
| ST6Gal I | Mammalian | NeuAcα2,6Galβ1,4GlcNAc- | 1 |
| ST3Gal III | Mammalian | NeuAcα2,3Galβ1,4GlcNAc- NeuAcα2,3Galβ1,3GlcNAc- | 1 |
| ST3Gal IV | Mammalian | NeuAcα2,3Galβ1,4GlcNAc- NeuAcα2,3Galβ1,3GlcNAc- | 1 |
| ST6Gal II | Photobacterium | NeuAcα2,6Galβ1,4GlcNAc- | 2 |
| ST3Gal V | N. meningitides N. gonorrhoeae | NeuAcα2,3Galβ1,4GlcNAc- | 3 |

1) Goochee et al. (1991) Bio/Technology 9: 1347–1355
2) Yamamoto et al. (1996) J. Biochem. 120: 104–110
3) Gilbert et al. (1996) J. Biol. Chem. 271: 28271–28276

The substrate specificity of the sialyltransferases is only the first criterion an enzyme must satisfy for establishing a method for sialylation of commercially important recombinant or transgenic glycoproteins. The sialyltransferase must also be able to effect sialylation efficiently and completely for a variety of glycoproteins, and support the scale-up to the 1–10 kg of recombinant glycoprotein with relatively low cost and infrastructure requirements. There are no published reports that document any of these sialyltransferases to be suitable for establishing a practical process that meets these requirements.

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1, 3GlcNAc or Galβ1,4GlcNAc glycoside (see, e.g., Wen et al. (1992) J. Biol. Chem., 267: 21011; Van den Eijnden et al. (1991) J. Biol. Chem., 256: 3159) and is responsible for sialylation of asparagine-linked oligosaccharides in glycoproteins. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al. (1982) J. Biol. Chem., 257: 13845); the human cDNA (Sasaki et al. (1993) J. Biol. Chem. 268:22782–22787; Kitagawa & Paulson (1994) J. Biol. Chem. 269:1394–1401) and genomic (Kitagawa et al. (1996) J. Biol. Chem. 271:931–938) DNA sequences are known, facilitating production of this enzyme by recombinant expression. In a preferred embodiment, the claimed sialylation methods use a rat ST3Gal III.

Other sialyltransferases, including those listed in Table 1, may also be useful in an economic and efficient large scale process for sialylation of commercially important glycoproteins. As a simple test to find out the utility of these other enzymes, various amounts of each enzyme (1–100 mU/mg protein) are reacted with asialo-$\alpha_1$ AGP (at 1–10 mg/ml) to compare the ability of the sialyltransferase of interest to sialylate glycoproteins relative to either bovine ST6Gal I, ST3Gal III or both sialyltransferases. Alternatively, other glycoproteins or glycopeptides, or N-linked oligosaccharides enzymatically released from the peptide backbone can be used in place of asialo-$\alpha_1$ AGP for this evaluation. Sialyltransferases showing an ability to sialylate N-linked oligosaccharides of glycoproteins more efficiently than ST6Gal I may prove useful in a practical large scale process for glycoprotein sialylation (as illustrated for ST3Gal III in this disclosure).

The invention also provides methods of altering the sialylation pattern of a glycoprotein by adding sialic acid in an α2,6Gal linkage as well as the α2,3Gal linkage, both of which are found on N-linked oligosaccharides of human plasma glycoproteins. In this embodiment, ST3Gal III and ST6Gal I sialyltransferases are both present in the reaction and provide proteins having a reproducible ratio of the two linkages formed in the resialylation reaction. Thus, a mixture of the two enzymes may be of value if both linkages are desired in the final product.

An acceptor for the sialyltransferase will be present on the glycoprotein to be modified by the methods of the present invention. Suitable acceptors include, for example, galactosyl acceptors such as Galβ1,4GlcNAc, Galβ1,4GalNAc, Galβ1,3GalNAc, lacto-N-tetraose, Galβ1,3GlcNAc, Galβ1, 3Ara, Galβ1,6GlcNAc, Galβ1,4Glc (lactose), and other acceptors known to those of skill in the art (see, e.g., Paulson et al. (1978) J. Biol. Chem. 253: 5617–5624). Typically, the acceptors are included in oligosaccharide chains that are attached to asparagine, serine, or threonine residues present in a protein.

In one embodiment, an acceptor for the sialyltransferase is present on the glycoprotein to be modified upon in vivo synthesis of the glycoprotein. Such glycoproteins can be sialylated using the claimed methods without prior modification of the glycosylation pattern of the glycoprotein. Alternatively, the methods of the invention can be used to alter the sialylation pattern of a glycoprotein that has been modified prior to sialylation. For example, to sialylate a protein that does not include a suitable acceptor, one can modify the protein to include an acceptor by methods known to those of skill in the art. The acceptor can be synthesized by attaching a galactose residue to, for example, a GlcNAc or other appropriate saccharide moiety that is linked to the protein. Glycoprotein-linked oligosaccharides can be first "trimmed," either in whole or in part, to expose either an acceptor for the sialyltransferase or a moiety to which one or more appropriate residues can be added to obtain a suitable acceptor. Enzymes such as glycosyltransferases and endoglycosidases are useful for the attaching and trimming reactions. The claimed methods are also useful for synthesizing a sialic acid-terminated saccharide moiety on a protein that is unglycosylated in its native form. A suitable acceptor for the sialyltransferase is attached to such proteins by methods known to those of skill in the art prior to sialylation using the methods of the present invention. See, e.g., U.S. Pat. No. 5,272,066 for methods of obtaining polypeptides having suitable acceptors for sialylation.

Thus, in one embodiment, the invention provides methods for in vitro sialylation of saccharide groups present on a glycoprotein that first involves modifying the glycoprotein to create a suitable acceptor. A preferred method for synthesizing an acceptor involves use of a galactosyltransferase. The steps for these methods include:

(a) galactosylating a compound of the formula GlcNR'β(1→3)Galβ-OR with a galactosyltransferase in the presence of a UDP-galactose under conditions sufficient to form the compound: Galβ(1→4)GlcNR'β1→3)Galβ-OR; and (b) sialylating the compound formed in (a) with a sialyltransferase in the presence of a CMP derivative of a sialic acid using an α(2,3)sialyltransferase under conditions in which sialic acid is transferred to the non-reducing sugar to form the compound: NeuAcα(2→3)Galβ(1→4)GlcNR'β(1→3)Galβ-OR. In this formula, R is an amino acid, a saccharide, an oligosaccharide or an aglycon group having at least one carbon atom. R' can be either acetyl or allyloxycarbonyl (Alloc). R is linked to or is part of a glycoprotein.

The galactosylating and sialylating steps are preferably carried out enzymatically, with the galactosylating step preferably being carried out as part of a galactosyltransferase cycle and the sialylating step preferably being carried out as part of a sialyltransferase cycle. Preferred conditions and descriptions of other species and enzymes in each of these cycles has been described. In a preferred embodiment, the galactosylating and sialylating steps are carried out in a single reaction mixture that contains both sialyltransferase and galactosyltransferase. In this embodiment, the enzymes and substrates can be combined in an initial reaction mixture, or preferably the enzymes and reagents for a second glycosyltransferase cycle can be added to the reaction medium once the first glycosyltransferase cycle has neared completion. By conducting two glycosyltransferase cycles in sequence in a single vessel, overall yields are improved over procedures in which an intermediate species is isolated. Moreover, cleanup and disposal of extra solvents and byproducts is reduced.

In a preferred embodiment, the sialylation of the glycoprotein is accomplished using a sialyltransferase cycle, which includes a CMP-sialic acid recycling system that utilizes CMP-sialic acid synthetase. CMP-sialic acid is relatively expensive, so in situ synthesis of this sialic acid donor moiety enhances the economic advantages provided by the claimed methods. Sialyltransferase cycles are described, for example, in U.S. Pat. No. 5,374,541. The CMP-sialic acid regenerating system used in this embodiment comprises cytidine monophosphate (CMP), a nucleoside triphosphate, a phosphate donor, a kinase capable of transferring phosphate from the phosphate donor to nucleoside diphosphates and a nucleoside monophosphate kinase capable of transferring the terminal phosphate from a nucleoside triphosphate to CMP.

The regenerating system also employs CMP-sialic acid synthetase, which transfers sialic acid to CTP. CMP-sialic acid synthetase can be isolated and purified from cells and tissues containing the synthetase enzyme by procedures well known in the art. See, for example, Gross et al. (1987) *Eur. J. Biochem.,* 168: 595; Vijay et al. (1975) *J. Biol. Chem.* 250: 164; Zapata et al. (1989) *J. Biol. Chem.* 264: 14769; and Higa et al. (1985) *J. Biol. Chem.* 260: 8838. The gene for this enzyme has also been sequenced. See, Vann et al. (1987) *J. Biol. Chem.,* 262:17556. Overexpression of the gene has been reported for use in a gram scale synthesis of CMP-NeuAc. See, Shames et al. (1991) *Glycobiology,* 1:187. This enzyme is also commercially available.

Nucleoside triphosphates suitable for use in accordance with the CMP-sialic acid regenerating system are adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleoside triphosphate is ATP.

Nucleoside monophosphate kinases are enzymes that catalyze the phosphorylation of nucleoside monophosphates. Nucleoside monophosphate kinase (NMK) or myokinase (MK; EC 2.7.4.3) used in accordance with the CMP-sialic acid regenerating system of the present invention are used to catalyze the phosphorylation of CMP. NMK's are commercially available (Sigma Chem. Co., St. Louis, Mo.; Boehringer Mannheim, Indianapolis, Ind.).

A phosphate donor and a catalytic amount of a kinase that catalyzes the transfer of phosphate from the phosphate donor to an activating nucleotide are also part of the CMP-sialic acid regenerating system. The phosphate donor of the regenerating system is a phosphorylated compound, the phosphate group of which can be used to phosphorylate the nucleoside phosphate. The only limitation on the selection of a phosphate donor is that neither the phosphorylated nor the dephosphorylated forms of the phosphate donor can substantially interfere with any of the reactions involved in the formation of the sialylated galactosyl glycoside. Preferred phosphate donors are phosphoenolpyruvate (PEP), creatin phosphate, and acetyl phosphate. A particularly preferred phosphate donor is PEP.

The selection of a particular kinase for use in a sialic acid cycle depends upon the phosphate donor employed. When acetyl phosphate is used as the phosphate donor, the kinase is acetyl kinase; creatin kinase is used for a creatin phosphate donor, and when PEP is used as the phosphate donor, the kinase is pyruvate kinase (PK; EC 2.7.1.40). Other kinases can be employed with other phosphate donors as is well known to those of skill in the art. Kinases are commercially available (Sigma Chem. Co., St. Louis, Mo.; Boehringer Mannheim, Indianapolis, Ind.).

Because of the self-contained and cyclic character of this glycosylation method, once all the reactants and enzymes are present, the reaction continues until the first of the stoichiometric substrates (e.g. free Neu5Ac and PEP, or the acceptor) is consumed.

In the sialylation cycle, CMP is converted to CDP by nucleoside monophosphate kinase in the presence of added ATP. ATP is catalytically regenerated from its byproduct, ADP, by pyruvate kinase (PK) in the presence of added phosphoenolpyruvate (PEP). CDP is further converted to CTP, which conversion is catalyzed by PK in the presence of PEP. CTP reacts with sialic acid to form inorganic pyrophosphate (PPi) and CMP-sialic acid, the latter reaction being catalyzed by CMP-sialic acid synthetase. Following sialylation of the galactosyl glycoside, the released CMP re-enters the regenerating system to reform CDP, CTP and CMP-sialic acid. The formed PPi is scavenged as discussed below, and forms inorganic phosphate (Pi) as a byproduct. Pyruvate is also a byproduct.

The byproduct pyruvate can also be made use of in another reaction in which N-acetylmannosamine (ManNAc) and pyruvate are reacted in the presence of NeuAc aldolase (EC 4.1.3.3) to form sialic acid. Thus, the sialic acid can be replaced by ManNAc and a catalytic amount of NeuAc aldolase. Although NeuAc aldolase also catalyzes the reverse reaction (NeuAc to ManNAc and pyruvate), the produced NeuAc is irreversibly incorporated into the reaction cycle via CMP-NeuAc catalyzed by CMP-sialic acid synthetase. This enzymatic synthesis of sialic acid and its 9-substituted derivatives and the use of a resulting sialic acid in a different sialylating reaction scheme is disclosed in International application WO 92/16640, published on Oct. 1, 1992.

As used herein, the term "pyrophosphate scavenger" refers to substances that serve to remove inorganic pyrophosphate from a reaction mixture of the present invention. Inorganic pyrophosphate (PPi) is a byproduct of the preparation of CMP-Neu5Ac. Produced PPi can feed back to inhibit other enzymes such that glycosylation is reduced. However, PPi can be degraded enzymatically or by physical means such as sequestration by a PPi binding substance. Preferably, PPi is removed by hydrolysis using inorganic pyrophosphatase (PPase; EC 3.6.1.1), a commercially available PPi catabolic enzyme (Sigma Chem. Co., St. Louis, Mo.; Boehringer Mannheim, Indianapolis, Ind.), and that or a similar enzyme serves as the pyrophosphate scavenger. One method of removing PPi or Pi from the reaction mixture is to maintain divalent metal cation concentration in the medium. In particular, the cations and the inorganic phosphate produced form a complex of very low solubility. By supplementing the cations which are lost by precipitation with pyrophosphate, the rate of reaction can be maintained and the reactions can be taken to completion (i.e., 100% conversion). Supplementing can be carried out continuously (e.g., by automation) or discontinuously. When cation concentration is maintained in this way, the transferase reaction cycle can be driven to completion.

For glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants. Preferably, the concentrations of activating nucleotides, phosphate donor, the donor sugar and enzymes are selected such that glycosylation proceeds until the acceptor is consumed, thus completely sialylating the saccharide groups present on the glycoprotein.

Enzyme amounts or concentrations are expressed in activity Units, which is a measure of the initial rate of catalysis. One activity Unit catalyzes the formation of 1 $\mu$mol of product per minute at a given temperature (typically 37° C.) and pH value (typically 7.5). Thus, 10 Units of an enzyme is a catalytic amount of that enzyme where 10 $\mu$mols of substrate are converted to 10 $\mu$mol of product in one minute at a temperature of 37° C. and a pH value of 7.5.

The above ingredients are combined by admixture in an aqueous reaction medium (solution). That medium has a pH value of about 6 to about 8.5. The medium is devoid of chelators that bind enzyme cofactors such as $Mg^{+2}$ or $Mn^{+2}$. The selection of a medium is based on the ability of the medium to maintain pH value at the desired level. Thus, in some embodiments, the medium is buffered to a pH value of about 7.5, preferably with HEPES. If a buffer is not used, the pH of the medium should be maintained at about 6 to 8.5, preferably about 7.2 to 7.8, by the addition of base. A suitable base is NaOH, preferably 6 M NaOH.

The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about zero degrees C to about 45° C., and more preferably at about 20° C. to about 37° C.

The reaction mixture so formed is maintained for a period of time sufficient for the desired percentage of terminal galactose residues present on saccharide groups attached to the glycoprotein to be sialylated. For commercial-scale preparations, the reaction will often be allowed to proceed for about 8–240 hours, with a time of between about 24 and 48 hours being more typical.

The following examples are offered to illustrate, but not to limit the present invention.

EXAMPLE 1

Sialylation of Recombinant Glycoproteins Using ST3Gal III

Several glycoproteins were examined for their ability to be sialylated by recombinant rat ST3Gal III. For each of these glycoproteins, sialylation will be a valuable process step in the development of the respective glycoproteins as commercial products.

Reaction Conditions

Reaction conditions were as summarized in Table 2. The sialyltransferase reactions were carried out for 24 hour at a temperature between room temperature and 37°. The extent of sialylation was established by determining the amount of $^{14}$C-NeuAc incorporated into glycoprotein-linked oligosaccharides.

Results and Discussion

The results presented in Table 2 demonstrate that a remarkable extent of sialylation was achieved in every case, despite low levels of enzyme used (essentially complete sialylation was obtained based on the estimate of available terminal galactose). Table 2 shows the amount of enzyme used per mg of protein (mU/mg) as a basis of comparison for the various studies. In several of the examples shown, only 7–13 mU ST3Gal III per mg of protein was required to give essentially complete sialylation after 24 hr.

These results are in marked contrast to those reported in detailed studies with bovine ST6Gal I where>50 mU/mg protein gave less than 50% sialylation, and 1070 mU/mg protein gave approximately 85–90% sialylation in 24 hr. Paulson et al. (1977) *J. Biol. Chem.* 252: 2363–2371; Paulson et al. (1978) i J. Biol. Chem. 253: 5617–5624. A study of rat α2,3 and α2,6 sialyltransferases by another group found that complete sialylation of asialo-α₁AGP required enzyme concentrations of 150–250 mU/mg protein. Weinstein et al. (1982) *J. Biol. Chem.* 257: 13845–13853. These earlier studies taken together suggested that the ST6Gal I sialyltransferase requires greater than 50 mU/mg and up to 150 mU/mg to achieve complete sialylation.

This Example demonstrates that sialylation of recombinant glycoproteins using the ST3 Gal III sialyltransferase requires much less enzyme than expected. For a one kilogram scale reaction, approximately 7,000 units of the ST3Gal III sialyltransferase would be needed instead of 100,000–150,000 units that the earlier studies indicated. Purification of these enzymes from natural sources is prohibitive, with yields of only 1–10 units for a large scale preparation after 1–2 months work. Assuming that both the ST6Gal I and ST3Gal III sialyltransferases are produced as recombinant sialyltransferases, with equal levels of expression of the two enzymes being achieved, a fermentation scale 14–21 times greater (or more) would be required for the ST6Gal I sialyltransferase relative to the ST3Gal III sialyltransferase. For the ST6Gal I sialyltransferase, expression levels of 0.3 U/1 in yeast has been reported. Borsig et al. (1995) *Biochem. Biophys. Res. Commun.* 210: 14–20. Expression levels of 1000 U/liter of the ST3 Gal III sialyltransferase have been achieved in *Aspergillus niger*. At current levels of expression 300–450,000 liters of yeast fermentation would be required to produce sufficient enzyme for sialylation of 1 kg of glycoprotein using the ST6Gal I sialyltransferase. In contrast, less than 10 liter fermentation of *Aspergillus niger* would be required for sialylation of 1 kg of glycoprotein using the ST3Gal III sialyltransferase. Thus, the fermentation capacity required to produce the ST3Gal III sialyltransferase for a large scale sialylation reaction would be 10–100 fold less than that required for producing the ST6Gal I; the cost of producing the sialyltransferase would be reduced proportionately.

EXAMPLE 2

Kinetics of Sialylation of Recombinant Glycoprotein Using ST3Gal III

Reaction Conditions

Assay mixtures (total volume of 500μl) consisted of: 25 mM MES pH6.0, 0.5% (v/v) Triton CF-54, 2 mg/ml BSA, 0.04% sodium azide, 1 mg neuraminidase treated-α1-acid glycoproteins, sialyltransferase (2–100 mUnit/ml), and 3400 nmole of CMP-sialic acid with a CMP-[$^{14}$C]SA tracer added to follow the extent of sialylation. The ST3Gal III was recombinantly produced, while the ST6Gal I was purified from bovine colostrum. The concentration of neuraminidase-treated α1-acid glycoprotein was determined by absorption using a predetermined extinction coefficient ($\epsilon$278=0.894 for 1 mg) and by the amount of terminal galactose as determined by the galactose dehydrogenase assay (Wallenfels and Kurz, G. (1966) *Meth. Enzymol.* 9: 112–116.).

After the indicated incubation times at 37° C., the extent of sialylation of neuraminidase treated al-acid glycoprotein was determined by removing 50 μl (10%) aliquots from the reaction mixture and glycoprotein acceptor was precipitated with 1 ml of 1% phosphotungstic acid in 0.5M HCl to separate it from CMP-SA donor. The pellet was washed twice with phosphotungstic acid followed by dissolving the pellet in 400 μl of chloroform/methanol 1:1 (v/v) of 4° C. for 20 minutes. After a final pellet was obtained by centrifugation, the supernatant was removed and the pellet allowed to dry. The pellet was then dissolved in 400 μl of 0.2M NaCl, 0.5N NaOH at 37° C. for 1 hr. The dissolved pellet was then transferred to scintillation vials for scintillation counting. Negative controls represented by omitting the acceptor were subtracted from each time point.

Results and Discussion

A time course of sialylation using ST3Gal III at a concentration of 20 mUnit/ml (10 mUnit/mg acceptor) is shown in FIG. 1. These results demonstrate that ST3Gal III efficiently sialylates open galactose residues on neuraminidase-treated α1-acid glycoprotein. In fact greater than 80% sialylation is achieved in one hour. The achievement of greater than 80% sialylation in one hour is significant in that

TABLE 2

Silaylation of recombinant glycoproteins using the ST3Gal III sialyltransferase

| | | Reaction Conditions | | | | Analytical Results | | | |
|---|---|---|---|---|---|---|---|---|---|
| | | Protein | | | | CMP-NeuAc | Terminal | NeuAc | |
| Protein | Source | Total (mg) | Conc. (mg/ml) | ST (mU/ml) | ST/Protein (mU/mg) | of 'cycle'[1] | Gal[2] mol/mol | Incorp.[3] mol/mol | % Rxn[4] | Other Characterization |
| ATIII[5] | Genzyme Transgenics | 8.6 | 4.3 | 210 | 48 | cycle | 1.2 | 1.4 | 117 | None |
| ATIII[5] | Genzyme Transgenics | 860 | 4.3 | 53 | 12 | cycle | 1.2 | 1.3 | 108 | SDS-gels: protein purity FACS: carbohydrate glycoforms |
| Asialo-fetuin | Sigma | 0.4 | 1.5 | 20 | 13 | 10 mM | 8.2 | 9.5 | 116 | None |
| asilao-[6] | PPL | 0.4 | 0.5 | 20 | 20 | 20 mM | 7 | 7.0 | 100 | SDS-gels: protein purity |

[1]'Cycle' refers to generation of CMP-NeuAc 'in situ' enzymatically using standard conditions as described in the specification (20 mM NeuAc and 2 mM CMP). The buffer was 0.1M HEPES, pH 7.5.
[2]Terminal (exposed) Gal content on N-linked oligosaccharides determined by supplier, or from literature values (fetuin, asialo-AAAT).
[3]NeuAc incorporated determined by incorporation of 14C-NeuAc after separation from free radiolabeled precursors by gel filtration.
[4]The % Rxn refers to % completion of the reaction based on the terminal Gal content as a theoretic maximum.
[5]Antitbrombin III.
[6]$_\alpha$1 Antitrypsin.

recombinant glycoproteins of therapeutic value may lose bioactivity with extended incubation times at 37° C.

Figure 2:
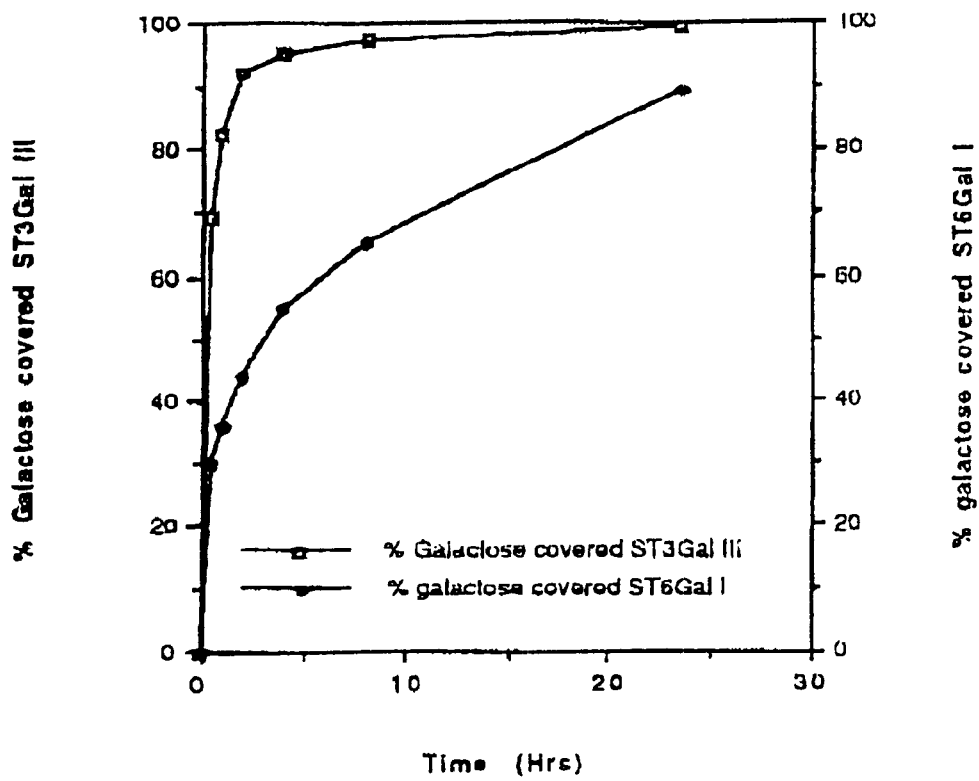
FIG. 2 shows a comparison of sialylation of neuraminidase-treated α1-acid glycoprotein using two different sialyltransferases, ST3Gal III and ST6 Gal I.

It should be noted that neuraminidase treated α1-acid glycoprotein is particularly difficult glycoprotein to completely sialylate due to the multiple tri- and tetra-antennary N-linked oligosaccharides. In fact, using neuraminidase treated α1-acid glycoprotein as an acceptor ST3Gal III, is superior to another common sialyltransferase, ST6Gal I isolated from bovine colostrum. A comparison of the sialylation capabilities of these two enzymes using neuraminidase treated α1-acid glycoprotein as an acceptor is shown in FIG. 2. These results demonstrate that ST3GalIII is superior to ST6Gal I at every time point examined, particularly with shorter incubation times. At one hour, ST3Gal III had sialylated 80% of the acceptors open galactose residues, while only 30% of the sites were saturated by ST6Gal I.

When different batches of neuraminidase treated α1-acid glycoprotein were used as acceptor utilizing similar assay conditions, the percent saturation of open galactose ranged from 75–99% for ST3Gal III and 42–60% for ST6Gal I at 24 hours. These results represent experiments in which ST3 Gal III and ST6Gal I are compared in parallel using identical conditions as defined above. For these experiments, neuraminidase treated α1-acid glycoprotein acceptor is separated from donor by gel filtration as described previously (Weistein et al. (1982) *J. Biol. Chem.* 257: 13845–13853).

In each case examined, ST3Gal III sialylated the acceptor to a level significantly greater than the extent of sialylation achieved with ST6Gal I up to 24 hours.

In addition to examining the above mammalian sialyltransferases, two bacterial sialyltransferases were examined for their ability to sialylate α1-acid glycoprotein. An unanticipated finding was that a recombinant 2,3 sialyltransferase from *Neisseria meningtidis* did not transfer sialic acid to α1-acid glycoprotein under conditions in which it sialylates oligosaccharides containing terminal Galβ1,4 such as LNnT and lactose. In contrast, a 2,6 sialyltransferase purified from *Photobacterium damsela* did efficiently incorporate sialic acid into neuraminidase treated α-acid glycoprotein as an acceptor.

EXAMPLE III

Identification of Sialyltransferases Useful in Methods for Practical Commercial Glycoprotein Modification Members of the mammalian sialyltransferase gene family shown in Table 3 below are expressed recombinantly and examined for their ability to sialylate a variety glycoproteins in a commercially practical manner.

TABLE 3

Mammalian Sialyltransferases

| Sialyltransferase | Sequences formed |
|---|---|
| ST3Gal I | Neu5Acα2,3Galβ1,3GalNAc |
| ST3Gal II | Neu5Acα2,3Galβ1,4GlcNAc |
| ST3Gal IV | Neu5Acα2,3Galβ1,4GlcNAc |
|  | Neu5Acα2,3Galβ1,3GlcNAc |
| ST5GalNAc I | Neu5Ac2,6GalNAc |
|  | Galβ1,3GalNAc(Neu5Acα2,6) |
|  | Galβ1,3GalNAc(Neu5Acα2,6) |
|  | Neu5Acα2,3Galβ1,3GalNAc(Neu5Acα2,6 |

TABLE 3-continued

Mammalian Sialyltransferases

| Sialyltransferase | Sequences formed |
|---|---|
| ST6GalNAc II | Neu5Ac2,6GalNAc |
|  | Galβ1,3GalNAc(Neu5Acα2,6) |
| ST6GalNAc III | Neu5Acα2,3Galβ1,3GalNAc(Neu5Acα2,6 |

Sialyltransferases capable of sialylating glycoproteins to a level of at least 80% using no more than 50 mUnits/mg of acceptor are considered "practical" for use in commercial-scale glycoprotein modification. The analysis utilizes assay conditions that are practical for use on a large scale, e.g., 1–10 mg/ml glycoprotein acceptor and a sialyltransferase concentration of (2–50 mUnit/mg of acceptor). The amount of open galactose is determined by the galactose dehydrogenase assay (Wallenfels et al., supra.). After appropriate incubation times at 37° C., the extent of glycoprotein is assessed by removing aliquots from the reaction mixture and separating the glycoprotein from CMP-SA donor by precipitation or by gel filtration.

Additionally, recombinant or purified sialyltransferases from bacteria displayed in Table 4 below can be examined. Again the sialyltransferase concentration do not exceed 50 mUnits/mg of glycoprotein acceptor and glycoprotein concentrations range from 1–10 mg/ml.

TABLE 4

Bacterial Sialyltransferases

| Sialyltransferase | Organism | Structure formed |
|---|---|---|
| Sialyltransferase | *N. meningitidis* | Neu5Acα2,3Galβ1,4GlcNAc |
|  | *N. gonorrheae* |  |
| ST3Gal VI | *Campylobacter jejuni* | Neu5Acα2,3Galβ1,4GlcNAc (also |
| ST3Gal VII | *Haemophilus somnus* | Neu5Acα2,3Galβ1,3GlcNAc) |
| ST3Gal VIII | *H. influenzae* |  |
| ST6Gal II | *Photobacterium damsela* | Neu5Acα2,6Galβ1,4GlcNAc |

The bacterial and mammalian sialyltransferases listed in Tables 3 and 4 are tested for their ability to fully sialylate the recombinant or transgenically expressed glycoproteins such as those displayed in Table 5 below. This list is not meant to be exhaustive but instead provides examples of glycoproteins of known therapeutic utility where complete sialylation may favorably alter the pharmacokinetics or biological activity of the glycoprotein. The glycoproteins used in these experiments can be produced in a transgenic animal, or in a eukaryotic cell or cell line.

In this experiment, the extent of sialylation and type of glycan modifying the glycoprotein of interest is examined using standard biochemical techniques such as gel electrophoresis, HPLC and mass spectrometry. This structural information is used to choose sialyltransferases with the correct specificity characteristics to completely (or as close as possible) sialylate the glycoprotein as judged by gel electrophoresis or HPLC of the resulting glycans. At this point the pharmacokinetics of the fully sialylated glycoprotein can be compared with the pharmacokinetics of the under-sialylated glycoprotein by examination in small animals.

It is recognized that certain glycoproteins will require a combination of sialyltransferases given the stereochemical and regioselective nature of this class of enzymes. Therefore, combinations of sialyltransferases are examined utilizing the defined conditions for their potential large scale practicality in remodeling glycoproteins. This is of particular importance when examining glycoproteins with both N-linked as well as O-linked glycans as well as those modified by highly branched oligosaccharides. In this regard, sialyltransferases that display multiple specificities such as the ST3Gal IV and the Campylobacter sialyltransferase may be particularly useful as stand-alone remodeling enzymes when sialylating glycoproteins with multiple N and O-linked glycans.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 50 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Modified-si te
      (B) LOCATION: 43..44
      (D) OTHER INFORMATION: /product= "OTHER"
          /note= "Xaa at positions 43 and 44
          may be present or absent"

(xi) SEQUENCE DESCRIPTION: SEQ ID NO:1:

Arg Cys Ala Val Val Ser Ser Ala Gly Xaa X aa Xaa Xaa Xaa Xaa Xaa
1               5                   10                  15

Xaa Xaa Xaa Xaa Xaa Xaa Xaa Xaa Xaa Xaa X aa Xaa Xaa Xaa Xaa Xaa
            20                  25                  30

Xaa Xaa Xaa Xaa Xaa Xaa Xaa Xaa Xaa Xaa X aa Xaa Asp Val Gly Ser
        35                  40                  45

Lys Thr
    50

TABLE 5

Glycoprotein sialylation candidates.

α-1-anti-trypsin
Tissue plasminogen activator
Erythropoietin
Granulocyte-macrophage colony stimulating factor (GMCSF)
Anti-thrombin III
Human growth hormone
Human interleukin 6
Interferon β
Protein C
Fibrinogen
Factor IX
Factor VII
Tumor necrosis factor
Tumor necrosis factor receptor protein

What is claimed is:

1. A large-scale method of sialylating a saccharide group on a recombinant glycoprotein, the method comprising contacting a saccharide group which comprises a galactose or N-acetylgalactosamine acceptor moiety on a recombinant glycoprotein with a sialic acid donor moiety and a recombinant sialyltransferase in a reaction mixture which provides reactants required for sialyltransferase activity for a sufficient time and under appropriate conditions to transfer sialic acid from said sialic acid donor moiety to said saccharide group wherein at least about 80% of the saccharide groups are sialylated, and wherein said recombinant sialyltransferase is present at 50 mU or less per mg of said recombinant glycoprotein.

2. The method of claim 1, wherein the sialic acid donor moiety is CMP-sialic acid.

3. The method of claim 2, wherein the CMP-sialic acid is enzymatically generated in situ.

4. The method of claim 1, wherein the sialyltransferase is a recombinant eukaryotic sialyltransferase which substantially lacks a membrane-spanning domain.

5. The method of claim 1, wherein the sialyltransferase includes a sialyl motif which has an amino acid sequence that is at least about 40% identical to a sialyl motif from a sialyltransferase selected from the group consisting of ST3Gal I, ST6Gal I, and ST3Gal III.

6. The method of claim 1, wherein the sialyltransferase is a recombinant ST3Gal III.

7. The method of claim 6, wherein the sialyltransferase is a recombinant rat ST3Gal III.

8. The method of claim 1, wherein the sialyltransferase is a recombinant ST3Gal IV.

9. The method of claim 1, wherein the sialyltransferase is a recombinant ST6Gal I.

10. The method of claim 1, wherein the sialyltransferase is a recombinant ST3Gal I.

11. The method of claim 10, wherein the reaction mixture comprises a second recombinant sialyltransferase, which second recombinant sialyltransferase is an ST3Gal III.

12. The method of claim 1, wherein the sialyltransferase is a recombinant bacterial sialyltransferase.

13. The method of claim 12, wherein the bacterial sialyltransferase has an amino acid sequence which is at least 50% identical to an amino acid sequence of a *Neisseria meningitidis* 2,3-sialyltransferase.

14. The method of claim 13, wherein the bacterial sialyltransferase is a *Neisseria meningitidis* 2,3-sialyltransferase.

15. The method of claim 12, wherein the bacterial sialyltransferase has an amino acid sequence which is at least 50% identical to an amino acid sequence of a *Photobacterium damsela* 2,6-sialyltransferase.

16. The method of claim 15, wherein the bacterial sialyltransferase is a *Photobacterium damsela* 2,6-sialyltransferase.

17. The method of claim 12, wherein the bacterial sialyltransferase has an amino acid sequence which is at least 50% identical to an amino acid sequence of a Haemophilus 2,3-sialyltransferase.

18. The method of claim 17, wherein the sialyltransferase is a Haemophilus 2,3-sialyltransferase.

19. The method of claim 12, wherein the bacterial sialyltransferase has an amino acid sequence which is at least 50% identical to an amino acid sequence of a *Campylobacter jejuni* 2,3-sialyltransferase.

20. The method of claim 19, wherein the sialyltransferase is a *Campylobacter jejuni* 2,3-sialyltransferase.

21. The method of claim 1, wherein the sialyltransferase is produced by recombinant expression of a sialyltransferase in a host cell selected from the group consisting of an insect cell, a mammalian cell, and a fungal cell.

22. The method of claim 21, wherein the host cell is an *Aspergillus niger* cell.

23. A large-scale method of sialylating a saccharide group on a recombinant glycoprotein, the method comprising contacting a saccharide group which comprises a galactose or an N-acetylgalactosamine acceptor moiety on a recombinant glycoprotein with a sialic acid donor moiety and a bacterial sialyltransferase in a reaction mixture which provides reactants required for sialyltransferase activity for a sufficient time and under appropriate conditions to transfer sialic acid from said sialic acid donor moiety to said saccharide group and wherein at least about 80% of the saccharide groups are sialylated, wherein said bacterial sialyltransferase is present at 50 mU or less per mg of said recombinant glycoprotein.

24. The method of claim 23, wherein the bacterial sialyltransferase has an amino acid sequence which is at least 50% identical to an amino acid sequence of a *Photobacterium damsela* 2,6-sialyltransferase.

25. The method of claim 24, wherein the bacterial sialyltransferase is a *Photobacterium damsela* 2,6-sialyltransferase.

26. The method of claim 23, wherein the bacterial sialyltransferase has an amino acid sequence which is at least 50% identical to an amino acid sequence of a *Neisseria meningitidis* 2,3-sialyltransferase.

27. The method of claim 26, wherein the sialyltransferase is a *Neisseria meningitidis* 2,3-sialyltransferase.

28. The method of claim 23, wherein the bacterial sialyltransferase has an amino acid sequence which is at least 50% identical to an amino acid sequence of a *Campylobacter jejuni* 2,3-sialyltransferase.

29. The method of claim 28, wherein the sialyltransferase is a *Campylobacter jejuni* 2,3-sialyltransferase.

30. The method of claim 23, wherein the bacterial sialyltransferase has an amino acid sequence which is at least 50% identical to an amino acid sequence of a Haemophilus 2,3-sialyltransferase.

31. The method of claim 30, wherein the sialyltransferase is a Haemophilus 2,3-sialyltransferase.

32. A large-scale method for in vitro sialylation of saccharide group s present on a glycoprotein, said method comprising contacting said saccharide groups with a sialyltransferase, a sialic acid donor moiety, and other reactants required for sialyltransferase activity for a sufficient time and under appropriate conditions to transfer sialic acid from said sialic acid donor moiety to said saccharide group, wherein said sialyltransferase is present at a concentration about 50 mU per mg of glycoprotein or less, and wherein at least about 80% of the saccharide groups are sialylated.

33. The method of claim 32, wherein the sialyltransferase is present at a concentration of between about 5–25 mU per mg of glycoprotein.

34. The method of claim 32, wherein the sialyltransferase is present at a concentration of between about 10–50 mU/ml of reaction mixture and the glycoprotein is present in the reaction mixture at a concentration of at least about 2 mg/ml.

35. The method of claim 32, wherein the method yields a glycoprotein having sialylation of at least about 80% of terminal galactose residues present on the saccharide groups.

36. The method of claim 32, wherein the sialyltransferase is a recombinant sialyltransferase.

37. The method of claim 36, wherein the sialyltransferase substantially lacks a membrane-spanning domain.

38. The method of claim 32, wherein the sialyltransferase includes a sialyl motif which has an amino acid sequence that is at least about 40% identical to a sialyl motif from a sialyltransferase selected from the group consisting of ST3Gal I, ST6Gal I, and ST3Gal III.

39. The method of claim 32, wherein the sialyltransferase is an ST3Gal III.

40. The method of claim 39, wherein the ST3Gal III is a rat ST3Gal III.

41. The method of claim 32, wherein the sialyltransferase is an ST3Gal IV.

42. The method of claim 32, wherein the sialyltransferase is an ST3Gal I.

43. The method of claim 42, wherein the reaction mixture comprises a second recombinant sialyltransferase, which second recombinant sialyltransferase is an ST3Gal III.

44. The method of claim 32, wherein the sialyltransferase is a bacterial sialyltransferase.

45. The method of claim 44, wherein the bacterial sialyltransferase is a recombinant sialyltransferase.

46. The method of claim 44, wherein the bacterial sialyltransferase has an amino acid sequence which is at least 50% identical to an amino acid sequence of a *Neisseria meningitidis* 2,3-sialyltransferase.

47. The method of claim 46, wherein the bacterial sialyltransferase is a *Neisseria meningitidis* 2,3-sialyltransferase.

48. The method of claim 44, wherein the bacterial sialyltransferase has an amino acid sequence which is at least 50% identical to an amino acid sequence of a *Photobacterium damsela* 2,6-sialyltransferase.

49. The method of claim 48, wherein the bacterial sialyltransferase is a *Photobacterium damsela* 2,6-sialyltransferase.

50. The method of claim 44, wherein the bacterial sialyltransferase has an amino acid sequence which is at least 50% identical to an amino acid sequence of a *Campylobacter jejuni* 2,3-sialyltransferase.

51. The method of claim 50, wherein the sialyltransferase is a *Campylobacter jejuni* 2,3-sialyltransferase.

52. The method of claim 44, wherein the bacterial sialyltransferase has an amino acid sequence which is at least 50% identical to an amino acid sequence of a Haemophilus 2,3-sialyltransferase.

53. The method of claim 52, wherein the sialyltransferase is a Haemophilus 2,3-sialyltransferase.

54. The method of claim 32, wherein the sialic acid donor moiety is CMP-sialic acid.

55. The method of claim 54, wherein the CMP-sialic acid is enzymatically generated in situ.

56. The method of claim 32, wherein the sialic acid is selected from the group consisting of NeuAc and NeuGc.

57. A large-scale method for in vitro sialylation of terminal galactose residues present on a glycoprotein, said method comprising contacting said glycoprotein with a reaction mixture that comprises a sialyltransferase, a sialic acid donor moiety, and other reactants required for sialyltransferase activity, for a sufficient time and under appropriate conditions to transfer sialic acid from said sialic acid donor moiety to said terminal galactose residues, wherein at least about 80% of the terminal galactose residues present on the glycoprotein are sialylated, and wherein said sialyltransferase is present at a concentration about 50 mU per mg of glycoprotein or less.

58. The method of claim 57, wherein the method further comprises contacting the saccharide groups with an ST6GalI sialyltransferase.

59. A large-scale method for in vitro sialylation of terminal galactose residues present on a glycoprotein, said method comprising contacting said glycoprotein with a reaction mixture that comprises a sialyltransferase, a sialic acid donor moiety, and other reactants required for sialyltransferase activity, for a sufficient time and under appropriate conditions to transfer sialic acid from said sialic acid donor moiety to said terminal galactose residues, wherein a greater percentage of terminal galactose residues are sialylated compared to an unaltered glycoprotein, wherein said greater percentage is equal to at least about 80%, and wherein said sialyltransferase is present at a concentration about 50 mU per mg of glycoprotein or less.

60. The method of claim 59, wherein at least 90% of the terminal galactose residues present on the glycoprotein are sialylated.

61. The method of claim 59, wherein the terminal galactose residues comprise one or more saccharides selected from the group consisting of Galβ1,4GlcNAc, Galβ1,4GalNAc, Galβ1,3GalNAc, Galβ1,3GlcNAc, Galβ1,3Ara, Galβ1,6GlcNAc, and Galβ1,4Glc.

62. The method of claim 61, wherein the terminal galactose residues comprise Galβ1,4GlcNAc or Galβ1,3GlcNAc.

63. The method of claim 62, wherein at least 80% of the terminal Galβ1,4GlcNAc residues present on the glycoprotein are sialylated.

64. The method of claim 62, wherein at least 80% of the terminal Galβ1,3 GlcNAc residues present on the glycoprotein are sialylated.

65. The method of claim 59, wherein the terminal galactose residues are present on an O-linked oligosaccharide.

66. The method of claim 59, wherein the terminal galactose residues are present on an N-linked oligosaccharide.

67. The method of claim 59, wherein the sialyltransferase includes a sialyl motif which has an amino acid sequence that is at least about 40% identical to a sialyl motif from a sialyltransferase selected from the group consisting of ST3Gal I, ST6Gal I, and ST3Gal III.

68. The method of claim 67, wherein the sialyltransferase is an ST3Gal III.

69. The method of claim 68, wherein the sialyltransferase is a rat ST3Gal III.

70. The method of claim 67, wherein the sialyltransferase is an ST3Gal IV.

71. The method of claim 67, wherein the sialyltransferase is an ST6Gal I.

72. The method of claim 67, wherein the sialyltransferase is an ST3Gal I.

73. The method of claim 59, wherein the sialyltransferase is a bacterial sialyltransferase.

74. The method of claim 73, wherein the bacterial sialyltransferase has an amino acid sequence which is at least 50% identical to an amino acid sequence of a *Neisseria meningitidis* 2,3-sialyltransferase.

75. The method of claim 74, wherein the bacterial sialyltransferase is a *Neisseria meningitidis* 2,3-sialyltransferase.

76. The method of claim 73, wherein the bacterial sialyltransferase has an amino acid sequence which is at least 50% identical to an amino acid sequence of a *Photobacterium damsela* 2,6-sialyltransferase.

77. The method of claim 76, wherein the bacterial sialyltransferase is a *Photobacterium damsela* 2,6-sialyltransferase.

78. The method of claim 73, wherein the bacterial sialyltransferase has an amino acid sequence which is at least 50% identical to an amino acid sequence of a Haemophilus 2,3-sialyltransferase.

79. The method of claim 78, wherein the sialyltransferase is a Haemophilus 2,3-sialyltransferase.

80. The method of claim 73, wherein the bacterial sialyltransferase has an amino acid sequence which is at least 50% identical to an amino acid sequence of a *Campylobacter jejuni* 2,3-sialyltransferase.

81. The method of claim 80, wherein the sialyltransferase is a *Campylobacter jejuni* 2,3-sialyltransferase.

82. The method of claim 59, wherein the glycoprotein comprises a moiety derived from an immunoglobulin.

83. The method of claim 82, wherein the immunoglobulin is an IgG.

84. The method of claim 1 or 23, wherein said recombinant glycoprotein is present at a concentration of at least about 2 mg/ml.

85. The method of claim 32, 57 or 59, wherein said glycoprotein is present at a concentration of at least about 2 mg/ml.

86. The method of claim 1 or 23, wherein said recombinant glycoprotein is present at a concentration of about 1–10 mg/ml.

87. The method of claim 32, 57 or 59, wherein said glycoprotein is present at a concentration of about 1–10 mg/ml.

* * * * *